Figure 1:
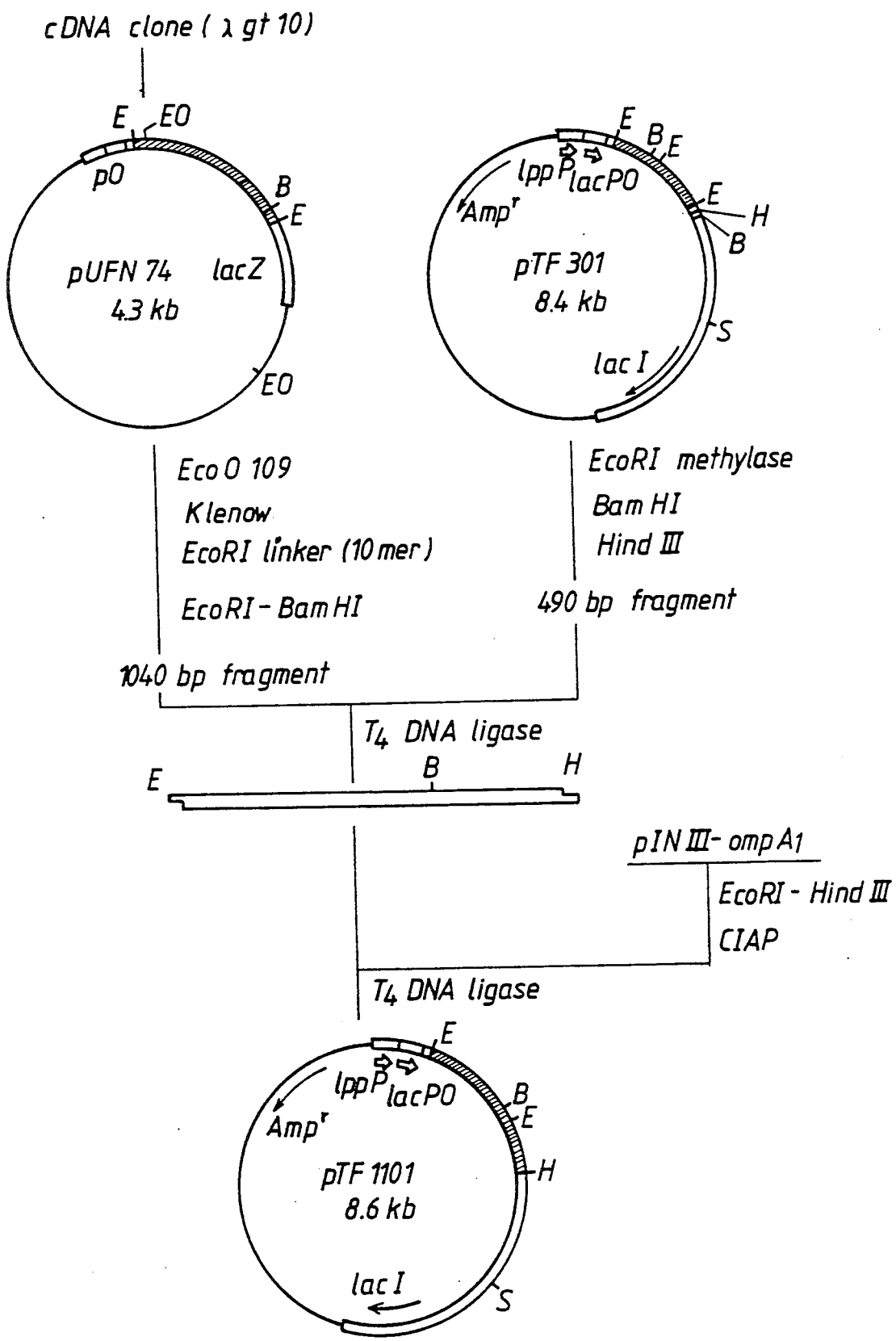

United States Patent [19]
Hashino et al.

[11] Patent Number: 5,136,023
[45] Date of Patent: * Aug. 4, 1992

[54] POLYPEPTIDE WITH CELL-SPREADING ACTIVITY

[75] Inventors: Kimikazu Hashino, Takatsuki; Shouichi Goto, Tushima; Yasutoshi Kawase, Otsu; Yoh'ichi Ohdate, Amagasaki; Yuki Taguchi, Otsu; Tatsuru Kinoshita, Kyoto; Fusao Kimizuka, Ohmihachiman; Ikunoshin Kato, Uji, all of Japan

[73] Assignee: Takara Shuzo Co., Ltd., Kyoto, Japan

[*] Notice: The portion of the term of this patent subsequent to Sep. 3, 2008 has been disclaimed.

[21] Appl. No.: 437,556

[22] Filed: Nov. 16, 1989

[30] Foreign Application Priority Data

Dec. 2, 1988 [JP] Japan .................. 63-305820

[51] Int. Cl.$^5$ ............................. C07K 13/00
[52] U.S. Cl. ..................... 530/350; 530/395
[58] Field of Search ..................... 530/350, 395

[56] References Cited

FOREIGN PATENT DOCUMENTS 0207751 7/1987 European Pat. Off. .

OTHER PUBLICATIONS

Kornblihit et al. Embo J. 4(7):1755-1759 (1985).
K. Sekiguchi & S. Hakomori, "Functional Domain Structure of Fibronectin", Proc. Natl. Acad. Sci, U.S.A., 77, 2661-2665, May 1980.
M. D. Pierschbacher, E. G. Hayman & E. Ruoslahti, "Location of the Cell-Attachement Site in Fibronectin with Monoclonal Antibodies and Proteolytic Fragments of the Molecule", Cell, 26, 259-267, Oct. 1981.
M. D. Pierschbacher & E. Ruoslahti, "The Cell Attachment Domain of Fibronectin. Determinaton of the Primary Structure", J. Biol. Chem., 257, 9593-9597, Aug. 1982.
M. D. Pierschbacher, E. G. Hayman & E Ruoslahti, "Synthetic Peptide with Cell Attachment Acitvity of Fibronection", Proc. Natl. Acad. U.S.A., 80, 1224-1227, Mar. 1983.
M. D. Pierschbacher & E. Ruoslahti, "Cell Attachment Activity of Fibronectin Can be Duplicated by Small Synthetic Fragments of the Molecule", Nature, 309, 30-33, May 1984.
A. R. Kornblihtt, K. Vibe-Pedersen & F. E. Baralle, "Human Fibronectin: Cell Specific Alternative mRNA Splicing Generates Polypeptide Chains Differing in the Number of Internal Repeats", Nucl. Acids Res., 12, 5853-5868, Jul. 1984.
M. D. Pierschbacher & E. Ruoslahti, "Variants of the Cell Recognition Site of Fibronectin thaat Retain Attachment-Promoting Activity", Proc. Natl. Acad. Sci. U.S.A., 81, 5985-5988, Oct. 1984.
A. R. Kornblihtt, K. Umezawa, K. Vibe-Pedersen & F. D. Baralle, "Primary Structure of Human Fibronectin: Differential Splicing May Generate at Least 10 Polypeptides from a Single Gene", EMBO J., 4, 1755-1759, 1985.
S. K. Akiyama, E. Hasegawa, T. Hasegawa & K. M. Yamada, "The Interaction of Fibronectin fragments with Fibroblascit Cells", J. Biol. Chem, 260, 13256-13260, Oct. 1985.
M. Obara, M. S. Kang, S. Rocher-Dufour, A. Kornblihtt, J. P. Thiery & K. M. Yamada, "Expression of the Cell-binding Domain of Human Fibronectin in *E. coli*", FEBS Lett., 213, 261-264, Mar. 1987.
Journal of Biological Chemistry, vol. 258, No. 5, Mar. 30th 1983, pp. 3332-3340, Wachington, DC US; M. Hayashi and K. M. Yamada: "Doman structure of the carboxyl-terminal half of human plasma fibronectin".
Journal of Biological Chemistry, vol. 260, No. 24, Oct. 26th 1986, pp. 13256-13260, Washington, DC, US; S. Akiyama et al.: "The interaction of fibronectin fragments with fibroblastic cells".

*Primary Examiner*—David L. Lacey
*Assistant Examiner*—Shelly J. Guest
*Attorney, Agent, or Firm*—Nikaido, Marmelstein, Murray & Oram

[57] ABSTRACT

A polypeptide having the cell-spreading activity of human fibronectin. Methods of preparing the polypeptide are described.

1 Claim, 1 Drawing Sheet

POLYPEPTIDE WITH CELL-SPREADING ACTIVITY

This invention relates to a protein that has cell-spreading activity like that of fibronectin. More particularly, the invention relates to a polypeptide which has the cell-spreading activity of fibronectin of human origin; and also to a method for the preparation of said polypeptide.

Fibronectin is a multifunctional glycoprotein which is widely distributed in a variety of animal tissues and body fluids and also on the surface of cultured cells and elsewhere This compound has various physiological effects, such as causing attachment, spreading, migration, differentiation, proliferation, and phagocytosis by cells, among others. This glycoprotein participates in such activities as tissue reconstruction, tissue construction, and protection from infection.

Fibronectin is a polypeptide with a molecular weight of about 250,000 and is a dimer with an S—S bond in the vicinity of the C-terminus. The amino acid sequence of this molecule contains 3 different types of internal repeats, and can be classified as types I, II and III. In addition, there are domain structures which have various functions, with the effect of cell attachment and spreading and the ability to bind to collagen, heparin, fibrin, etc. Of these domains, industrial applications of the biological activity related to the cell attachment and spreading domain have been considered; for example, in the preparation of a coating agent for a substrate for culture, it is possible to use this function in the preparation of a substrate to which cells will bind. Also, this function can be used as an accelerator of cell binding in such preparations as collyrium, lotions, and agents for the healing of wounds. Cell spreading is a phenomenon that follows after cell attachment. For cells to proliferate, with some exceptions, it is necessary for the phenomenon of spreading to take place, not cell attachment alone.

The basic structure which is the minimum essential structure for the cell-attachment domain of fibronectin is the sequence Arg-Gly-Asp-Ser (*Nature*, 309 1984, 30–33). Japanese Laid-Open Patent (Tokuhyo) 84–501548 discloses a peptide with cell-attachment activity, that is a polypeptide of the molecular weight of 11,500 and that contains this sequence among its sequence with 108 amino acid residues.

However, the cell-attachment activity of this polypeptide with the molecular weight of 11,500 is much weaker than that of fibronectin of natural origin, and it is not necessarily possible to make use of it in the practical applications mentioned above. This difficulty is discussed, for example, in *J. Biol. Chem.* 260 (1985), 13256–13260. Also, the inventors of this invention have constructed the polypeptide of the molecular weight of 11,500 mentioned above by means of genetic engineering, and compared its cell-spreading activity to that of fibronectin of natural origin with the use of normal rat kidney (NRK) cells. The results were that, whereas fibronectin gave noticeable activity at the dose of 0.1–1 μg/well, the dose of 50 μg/well of the polypeptide with the molecular weight of 11,500 did not have any such activity.

The object of this invention is to identify the amino acid sequence that has substantial cell-spreading activity as the peptide of the cell-spreading domain of fibronectin and to provide a method for producing the same.

Briefly the present invention relates to polypeptides with cell-spreading activity, which have an amino acid sequence represented by the following formula [I]:

```
Ala Pro Ile Val Asn Lys Val Val Thr Pro Leu Ser Pro Pro Thr Asn Leu His Leu Leu   [I]
Ala Asn Pro Asp Thr Gly Val Leu Thr Val Ser Trp Glu Arg Ser Thr Thr Pro Asp Ile
Thr Gly Tyr Arg Ile Thr Thr Thr Pro Thr Asn Gly Gln Gln Gly Asn Ser Leu Glu Glu
Val Val His Ala Asp Gln Ser Ser Cys Thr Phe Asp Asn Leu Ser Pro Gly Leu Glu Tyr
Asn Val Ser Val Tyr Thr Val Lys Asp Asp Lys Glu Ser Val Pro Ile Ser Asp Thr Ile
Ile Pro Ala Val Pro Pro Pro Thr Asp Leu Arg Phe Thr Asn Ile Gly Pro Asp Thr Met
Arg Val Thr Trp Ala Pro Pro Pro Ser Ile Asp Leu Thr Asn Phe Leu Val Arg Tyr Ser
Pro Val Lys Asn Glu Glu Asp Val Ala Glu Leu Ser Ile Ser Pro Ser Asp Asn Ala Val
Val Leu Thr Asn Leu Leu Pro Gly Thr Glu Tyr Val Val Ser Val Ser Ser Val Tyr Glu
Gln His Glu Ser Thr Pro Leu Arg Gly Arg Gln Lys Thr Gly Leu Asp Ser Pro Thr Gly
Ile Asp Phe Ser Asp Ile Thr Ala Asn Ser Phe Thr Val His Trp Ile Ala Pro Arg Ala
Thr Ile Thr Gly Tyr Arg Ile Arg His His Pro Glu His Phe Ser Gly Arg Pro Arg Glu
Asp Arg Val Pro His Ser Arg Asn Ser Ile Thr Leu Thr Asn Leu Thr Pro Gly Thr Glu
Tyr Val Val Ser Ile Val Ala Leu Asn Gly Arg Glu Glu Ser Pro Leu Leu Ile Gly Gln
Gln Ser Thr Val Ser Asp Val Pro Arg Asp Leu Glu Val Val Ala Ala Thr Pro Thr Ser
Leu Leu Ile Ser Trp Asp Ala Pro Ala Val Thr Val Arg Tyr Tyr Arg Ile Thr Tyr Gly
Glu Thr Gly Gly Asn Ser Pro Val Gln Glu Phe Thr Val Pro Gly Ser Lys Ser Thr Ala
Thr Ile Ser Gly Leu Lys Pro Gly Val Asp Tyr Thr Ile Thr Val Tyr Ala Val Thr Gly
Arg Gly Asp Ser Pro Ala Ser Ser Lys Pro Ile Ser Ile Asn Tyr Arg Thr Glu Ile Asp.
Lys Pro Ser Gln Met
```

This invention also relates to recombinant plasmids which contain the DNA which codes for the polypeptides with cell-spreading activity having the structure represented by the above formula [I], and this invention also relates to transformants which carry these recombinant plasmids. The present invention further relates to a method for the preparation of the polypeptides having the structure of the formula [I] with cell-spreading activity by the cultivation of these transformants and the collection of the polypeptides from the culture medium.

We have proceeded research on peptides with cell-spreading activity and have prepared a polypeptide with a sequence of 385 amino acids ($Ala^{1133}$-$Met^{1517}$) from cell-spreading domain of fibronectin (abbreviated FN below) by the techniques of genetic engineering. We found the polypeptide has about the same level of cell-spreading activity as FN.

This invention is based upon those findings.

In this specification, the superscript numerals affixed to the symbols for amino acids show the number of the amino acid residue counted from the N-terminus of the amino acids of FN based on the EMBL Data Bank.

The invention will be explained in more detail below.

Cloning of the cDNA fragment that codes for the peptide of FN with 504 amino acid residues is done as follows. First, it is possible to make a cDNA library that includes the cDNA region needed for FN by use of the primer extension method from poly (A)+ from human liver. Here, as the primer, a DNA oligomer complementary to the DNA sequence that coded for FN is used, and the library is obtained by use of, for example, the Gublar-Hoffman method. For the screening of the library, the plaque hybridization method with, for probe, a cDNA fragment for FN, such as, for example, pLF5 (Biochemistry, 25, 4936-4941, 1986), can be used. Phage DNA is isolated from plaques that are positive, and checking is done to be sure that the desired cDNA fragment is included therein. By the combination of this cDNA fragment with other cDNA fragments present (such as, for example, pLF5), it is possible to construct a plasmid such as pTF1101 that contains the cDNA fragment that codes for, for example, the cell-binding domain of FN from $Gly^{1014}$ to $Met^{1517}$, or another such plasmid that contains the cDNA fragment that codes for the desired amino acid sequence. Next, an appropriate restriction enzyme is used to cleave one site slightly upstream of the initiation codon of pTF1101 that codes for the sequence $Gly^{1014}$-$Met^{1517}$ of FN, and then exonuclease is used, by which means it is possible to the 5'-end of the sequence. By changes in the reaction conditions, it is possible to obtain a plasmid from which appropriate portions of the 5'-terminus of the coding region have been deleted. Then an appropriate restriction enzyme is used to cleave a site slightly downstream from the termination codon of the coding region of these plasmids, and the DNA which has been cleaved is separated by gel electrophoresis, by which it is possible to obtain fragments of cDNA from which various portions of the 5'-terminal strand have been removed. By the insertion of these cDNA fragments into an appropriate expression vector, it is possible to express peptides of various lengths wherein portions of the N-terminal region of the sequence of $Gly^{1014}$-$Met^{1517}$ (504 amino acid residues) have been deleted.

As the expression vector, any of the well-known vectors can be used. We have obtained satisfactory results with direct expression by the use of the pUC-type vectors in which the distance between the ribosome-binding site and the initiation codon has been made optimum.

Also, by the joining with a transcription-termination signal downstream from the termination (stop) codon of pUC vectors, it is possible to improve the expression level.

Selection of the recombinants which express the peptide with cell-spreading activity can be done conveniently with immunoscreening. That is, expression vectors to which the cDNA fragments of different lengths have been joined are inserted into cells of Escherichia coli by the usual methods, and the transformants obtained are raised on nitrocellulose filters, after which they are lysed, and the protein from the cells is fixed on the filters. After the filters are blocked with bovine serum albumin or the like, a monoclonal antibody which recognizes the domain of cell spreading of FN is caused to act. The monoclonal antibody bound to the filter is detected by labelling with a second antibody. In this way, it is possible to select recombinants that express the peptide with the domain for cell spreading.

Next, the recombinants so selected are cultured under conditions suitable for expression, and expression of the peptide with the domain for cell spreading is induced. For verification that expression is taking place, immunoblotting can be used. Thus, the whole-cell protein of the cultured cells is lysed by heat treatment in a buffer containing SDS, and separation is conducted on SDS-polyacrylamide electrophoresis, and the electrophoretic pattern is transferred to a nitrocellulose or nylon membrane. After a monoclonal antibody specific for the cell-spreading domain of FN is incubated with the membrane, an enzyme-labeled second antibody is applied, and the enzyme activity of the bound antibody gives rise to color in a chromagenic material, thereby it is possible to confirm that there is a band of the peptide with the cell-spreading domain.

Also by analysis of the base sequence of the 5'-end of the insert fragments of the clones that are obtained, it is possible to identify the N-terminus of the peptide that is expressed.

At the N-terminus of the peptide produced by a obtained in this way, there are attached a methionine residue that arises from the initiation codon of E. coli and an alanine residue that arises from the NcoI linker, but these residues do not affect the cell-spreading activity. However, it is possible to remove those extra sequences, as needed. For example, under the suitable condition, it is possible to remove the N-terminal methionine during the culture of the recombinant by the action of a methionine aminopeptidase which is usually produced in E. coli. This removal can also be accomplished with the use of methionine aminopeptidase on a partially purified peptide (J. Bacteriol., 169, 751, 1987). Also, it is possible to remove the alanine that arises from NcoI linker by the methods of site-specific mutagenesis.

Purification of the peptide with the domain for cell spreading from the recombinants can be done, for example, as follows. The cell pellet is suspended in a buffer, and the soluble fraction and insoluble fraction are separated by ultrasonification. The insoluble fraction is solubilized in a buffer which contains 7 M urea. The soluble fractions are pooled, and put on a Sepharose 4B column bound with the antibody used in immunoblotting; then, affinity purification is carried out. For elution there is used a buffer in the pH region of 2.3. By the collection of the desired fractions by immunoblotting, it is possible to collect the peptide with the domain for cell spreading. When necessary, further purification by FPLC and HPLC can be done.

The peptide with the cell-spreading domain thus obtained may be measured for its cell-spreading activity toward NRK (normal rat kidney) cells. The sample is dissolved in a buffer, and used to coat microtiter plate wells, after which NRK cells are added, and the plate is incubated for a fixed time at 37° C. The spreading of the cells is observed under a microscope, and the minimum dose of sample per well that gives rise to the expression of cell-spreading activity is compared to the dose needed of FN of natural origin. In this way, the strength of the cell-spreading activity can be expressed.

By the series of experiments described above, it has been found that the peptide with the sequence of 385 amino acids ($Ala^{1133}$-$Met^{1517}$ the sequence shown in general formula I shown above has essentially the same cell-spreading activity as that of FN.

The invention will be further explained in more detail by the following Examples, which partly refer to the accompanying drawings wherein;

FIG. 1 is a diagram of the processes involved in the construction of an expression plasmid which carries the DNA sequence which codes for the polypeptide including the $Gly^{1014}$-$Met^{1517}$ sequence of fibronectin.

EXAMPLE 1

Construction of recombinants (1) Construction of the expression plasmid pTF1101 which codes for Gly$^{1014}$-Met$^{1517}$ (504 amino acid residues) of fibronectin (See FIG. 1)

FIG. 1 is a diagram of the processes involved in the construction of an expression plasmid which carries the DNA sequence which codes for the polypeptide including the Gly$^{1014}$-Met$^{1517}$ sequence of fibronectin.

(1-1) Synthesis of the primer-extended cDNA

The 17-base synthetic primer (5' GTCTCCACT-GAAGTGC3') that is the complementary sequence to the mRNA of fibronectin was prepared by use of a DNA synthesizer (Applied Biosystems, Inc., type 380A). This synthetic primer was used to synthesize cDNA from poly(A+)RNA of human origin (from Clontec Laboratories, Inc.).

In the synthesis of cDNA, reagents from the cDNA synthesis system of Amersham were used. These included 4 μl of 5×buffer for the synthesis of the first strand, 1 μl of sodium pyrophosphate solution, 1 μl of ribonuclease inhibitor (20 units), 2 μl of a mixture of deoxyribonucleotide triphosphate (10 mM), 1 μl of synthetic DNA primer (0.1 μg), 5 μCi of [α-$^{32}$p]dCTP, and 1 μl of poly(A+)RNA (1 μg), which reagents were added in this order to a cooled Eppendorf tube, the contents of which were gently mixed. Then 20 units of reverse transcriptase 1 μg) and distilled water were added to the tube to bring the total volume to 20 μl, and the contents were gently mixed. The mixture was incubated for 50 minutes at 42° C. The tube was returned to an ice-bath and the following were added, in this order: 37.5 μl of a buffer for use in synthesis of the second strand, 50 μCi of [α-$^{32}$P]dCTP (5 μl), 0.8 unit of ribonuclease H from *Escherichia coli* (1 μl ), 23 units of *Escherichia coli* DNA polymerase 1 (3.5 μl ), and 33 μl of water. The contents of the tube were gently mixed. The tube was incubated first for 60 minutes at 12° C., then for 60 minutes at 22° C., and then for 10 minutes at 70° C., before being returned to an ice-bath. Then 2.0 units (0.5 μl ) of T4 DNA polymerase was added. After gentle mixing of the contents, the tube was incubated for 10 minutes at 37° C. Then the reaction was stopped by the addition of 10 μl of 0.25 M EDTA (pH 8.0) and 10 μl of 10% SDS. Phenol extraction was twice, and then an equal volume of 4 M ammonium acetate wa added, followed by the addition of two volumes of cooled ethanol. The mixture was left for 15 minutes in dry ice, and then returned to room temperature. The mixture was centrifuged for 10 minutes and the supernatant removed. The pellet was dissolved in 50 μl of TE (10 mM Tris-HCl and 1 mM EDTA, pH 8.0), and ethanol precipitation was repeated once more. The precipitate was washed in 200 ul of cooled ethanol, dried, and dissolved in a small amount of TE.

(1-2) Ligation of cDNA with the πgt 10 phage vector and in vitro packaging

The cDNA obtained in section (1-1) above was put into 16.6 μl of a reaction mixture which contains 0.5 μg of EcoRI linker (d[pGGAATTCC]), ligation buffer and 2.8 units of T4 DNA ligase, and the mixture was incubated overnight at 15° C. Then the reaction was stopped by treatment for 10 minutes at 70° C. The buffer was changed to one suitable for the reaction of EcoRI, and 50 units of EcoRI was added; the total volume brought to 100 μl before incubation for 2 hours at 37° C. Then the reaction was stopped by treatment for 10 minutes at 70° C. The entire mixture was put on a Sephadex G-50 column (1 ml) and the column was eluted with STE buffer (100 mM NaCl, 10 mM Tris-HCl, and 1 mM EDTA, pH 8.0). The free linker was removed in this way. Then the cDNA fraction was dialyzed against 10 mM Tris-HCl (pH 8.0) and 0.1 mM EDT, after which it was lyophilized. To the resultant substance were added 333 mM NaCl and 10 mM MgCl$_2$, and the mixture was made to 4.5 μl, after which 0.5 μl (0.25 μg) of λgt 10/EcoRI Arms (Amersham) was added, followed by 5 μl of solution B from a DNA ligation kit (Takara Shuzo). The mixture was incubated for 10 minutes at 26° C., and the reaction was stopped by treatment for 10 minutes at 70° C. This allows an in vitro packaging reaction to take place. Into 4 μl of reaction fluid, two kinds of packaging extracts (Stratagene) were gently mixed in, and incubation follows for 2 hours at 22° C., during which time phage particles were formed. Then 500 μl of SM buffer (100 mM NaCl, 8 mM MgSO$_4$, 50 mM Tris-HCl, pH 7.5, and 0.01% gelatin) were added with 20 μl of chloroform, and the mixture was kept at 4° C.

(1-3) Plaque hybridization

First, 100 μl of the mixture prepared above was added to 200 μl of a *Escherichia coli* NM 514 culture which had been cultured overnight on L-broth plus 4% maltose, and this was incubated for 15 minutes at 37° C. Then, 4 ml of L soft agar medium (L-broth plus 8% agar) heated to 42° C. was added before it was overlayed on top of 20 ml of L-agar plate. This culture was incubated overnight at 37° C. and the nylon filters (Hybond N, Amersham) were placed on top of the plates for 30 seconds. The filters were placed for 5 minutes on top of thick filter paper that had been saturated with denaturing solution (0.5 M NaOH and 1.5 M NaCl); then, they were placed for 5 minutes on top of thick filter paper that had been saturated with neutralizing solution (0.5 M Tris-HCl, pH 7.0, and 1.5 M NaCl). Next, the filters were washed with 2×SSC (0.3 M NaCl and 30 mM sodium citrate, pH 7.0) and dried. They were fixed with ultraviolet ;illumination at 300 nm for 5 minutes, and used as replica filters. Separately, a probe for use in hybridization was prepared. First, 4 μg of the plasmid pLF5 was digested with 12 units of PvuII, and next with 15 units of EcoRI, and 100 ng of the resulting 0.43-kb fragment was obtained by agarose electrophoresis. The fragment obtained was labelled with $^{32}$P by use of the multiprime DNA labelling system of Amersham according to the attached protocol. The labelled probe thus obtained had an activity of 5.5 10$^7$ cpm per 60 μl. The replica filters mentioned above were put into 15 ml of a solution which contains 6×SSC, 5×Denhardt (0.1% BSA, 0.1% polyvinylpyrrolidone, and 0.1% Ficoll), 0.5% SDS, and 80 μg/ml salmon sperm DNA, and the whole was incubated for 4 hours at 65° C., during which time prehybridization occurred. Next, labelled probe (2.75×10$^7$ dpm) which had been heat-denatured was added to the mixture, and hybridization was allowed to take place overnight under the same conditions. The filters were washed twice in 2×SSC and 11 0.1% SDS for 15 minutes at 65° C. and then washing was done twice in 0.2×SSC and 0.1% SDS for 15 minutes at 65° C. 2×SSC was used for a brief rinse, and autoradiography was was conducted. The result was the finding of a radioactive signal in 250 of the $4 \times 10^3$ plaques.

(1-4) Preparation of phage DNA and analysis of inserted fragments

Phage clones which gave a positive signal were suspended in 1 ml of SM buffer, and 250 ul of this suspension was added to 0.5 ml of a culture of *Escherichia coli* NM514 cells which had been cultured overnight. The mixture was incubated for 15 minutes at 37° C., and the phages allowed to attach; 5 ml of L-broth containing 10 mM MgCl$_2$ was added, and culture was carried out for 4.5 hours at 37° C. with shaking. To the culture was added 50 μl of chloroform, and shaking was continued for 10 minutes. Then the culture was centrifuged and the supernatant (the phage lysate) was obtained. Then, to the phage lysate, 20 μg of DNase I and 10 μg of RNase A were added, and the mixture was incubated for 3 minutes at 37° C. Then 0.29 g of NaCl was added together with 0.55 g of PEG 6000, and the mixture was incubated over ice for 2 hours. The let was obtained from centrifugation of this mixture, and suspended in 400 μl of TE. Phenol extraction was conducted twice, phenol/chloroform extraction was conducted once, and chloroform extraction was conducted once, after which ethanol precipitation was performed. In this way, phage DNA was obtained. The phage DNA was dissolved in 20 μl of TE, and put into 30 μl of a reaction mixture containing 20 units of EcoRI; the mixture was incubated for 2 hours at 37° C. The inserted fragments were analyzed by the use of agarose electrophoresis. The results were that, of the 24 clones, one clone was found to have a 1.1-kb inserted fragment. This 1.1-kb fragment was subcloned into the plasmid pUC118, and the recombinant plasmid obtained was designated pUFN74. This plasmid was used in the identification by the dideoxy method of the base sequence of the inserted fragment. It was found that this fragment was the cDNA of fibronectin (EMBO Journal, 4[1985], 1755–1759), starting from the G in the 2990th position to the A in the 4105th position. However, the C in the 3018th position, the C in the 3063th position, and the C in the 3216th position were replaced by A, A, and T, respectively; however, there was no change in the amino acids coded for.

(1-5) Preparation of Eco0109BamHI fragment of pUFN74

Per 40 μg of pUFN74, 200 units of Eco0109 was added, and in a reaction mixture of 400 μl, these were incubated for 2 hours at 37° C. Then ethanol precipitation was used to collect the DNA. Half of the DNA obtained was put into 200 μl of a reaction mixture which contains 7 mM Tris-HCl, pH 7.5, 1 mM EDTA, 20 mM NaCl, 7 mM MgCl$_2$, 20 μM dATP, 20 μM dGTP, 20 μM dCTP, 20 μM dTTP, and 2 units of Klenow fragment. This mixture was incubated for 20 minutes at room temperature. Then the reaction was stopped by treatment for 10 minutes at 65° C., and the reaction mixture was given the composition of ligation buffer followed by the addition of 2.5 nmol of EcoRI linker (d[pCCGAATTCGG]) and 2.8 units of T4 DNA ligase. This mixture was incubated overnight at 13° C. The reaction was stopped by heating of the mixture. This was put into 400 μl of a reaction mixture containing 60 units of BamHI and 50 units of EcoRI, and the whole was incubated for 2 hours at 37° C. Then a 1.0-kb fragment was obtained by agarose electrophoresis; the yield was 0.2 μg.

(1-6) Preparation of BamHI-HindIII fragment of pTF301

First, 200 units of EcoRI methylase was added to 50 μg of PTF301 (constructed by the method in Japanese Laid-Open Patent (Tokkai) 89-180900, U.S. patent application No. 07/291,894 (Dec. 29, 1988)), and this was made to 200 μl the reaction mixture was incubated for 1 hour at 37° C. Then the mixture was treated for 20 minutes at 65° C., and made to 400 μl. To the reaction mixture were added 60 units of BamHI and 60 units of HindIII. The mixture was incubated for 2 hours at 37° C. Then a 0.5-kb fragment was obtained by agarose electrophoresis; the yield was 0.1 μg.

(1-7) Construction and cloning of cDNA fragments which code for Gly$^{1014}$-Met$^{1517}$ (504 amino acid residues)

First, 0.2 μg of the 1.0-kb fragment obtained in section (1-5) above and 0.1 μg of the 0.5-kb fragment obtained in section (1-6) above were put into 100 μl of a ligation buffer, to which 2.8 units of T4 DNA ligase was added, and the whole was incubated overnight at 16° C. before being heat-treated at 70° C. for 10 minutes to stop the reaction. The reaction mixture was made into a buffer for the use of HindIII, and 100 μl of the reaction mixture containing 12 units of HindIII was incubated for 2 hours at 37° C. Then, the buffer was made into a buffer for the use of EcoRI, and 10 units of EcoRI was added, and the whole was incubated for 2 hours at 37° C. The reaction was stopped by heating. Then 20 μl of this reaction mixture was added to 30 μl of a reaction mixture containing 0.16 μg of dephosphorylated plasmid pIN-III-ompA-1 treated with EcoRI-HindIII and 2.8 units of T4 DNA ligase. This mixture was incubated overnight at 16° C. Half of the reaction mixture was used for the transformation of *Escherichia coli* HB101 cells. Of the transformants obtained, 12 clones were studied for the inserted fragments that they contained. Five of the clones contained 1.5-kb fragment. Their base sequences were identified by the dideoxy method, and a plasmid that contained the cDNA that codes for the Gly$^{1014}$-Met$^{1517}$ sequence of fibronectin was found. This plasmid was named pTF1101, and the *Escherichia coli* JM109 cells that carry the plasmid were designated JM109/pTF1101. The strain was deposited at the Fermentation Research Institute of the Agency of Industrial Science and Technology, Japan, under FERM BP-2156.

(2) Preparation of DNA fragments

First, 40 μg of plasmid pTF1101 mentioned above as coding for the cell-adhesive polypeptide that has a sequence of 504 amino acid residues was incubated for 2 hours at 37° C. in 102 μl of a reaction mixture that contained 24 units of the restriction enzyme XbaI in a buffer for use with this restriction enzyme, and then the reaction was stopped by the heating of the reaction mixture at 65° C. for 5 minutes. The DNA was obtained by ethanol precipitation. Half of the DNA obtained was incubated at 30° C. in 116 μl of a reaction mixture that contained 12 units of the BAL31 nuclease S in a buffer for use with this enzyme BAL31 nuclease S, and every 2 minutes from the second to the eighth minute of incubation, 23 μl of the reaction mixture was removed; to each portion, phenol was added to stop the reaction before the DNA in this portion was obtained by ethanol precipitation. Half of each of the amounts of DNA obtained in this was added to 40 μl of a reaction mixture that contained 0.4 unit of Klenow enzyme in a buffer for use with Klenow enzyme, and the reaction mixture was incubated at 37° C. for 20 minutes. The reaction was stopped by the heating of the reaction mixtures at 65° C. for 5 minutes. Then to half of each reaction mixture was added 10 μl of a solution that contained 1 μg of phosphorylated NcoI linker (d[AGCCAT-GGCT]), and to this mixture, 80 μl of liquid A and 20 μl of liquid B from a DNA ligation kit (Takara Shuzo Co., Ltd.) were added, and the resultant mixtures were incubated for 30 minutes at 16° C. Then 10 μl of each reaction mixture was used to transform cells of E. coli JM109. The transformants obtained were cultured overnight at 37° C. on a shake culture in 5 ml of L-broth that contained 50 μg/ml ampicillin. Cells were harvested from about 1.5 ml of the broth, and plasmid DNA was isolated and purified from each sample. The DNAs obtained were dissolved in 100 μl of TF. Then, 100 μl of each of the DNA solutions obtained in this way was incubated for 2 hours at 37° C in 126 μl of a reaction mixture that contained 12 units of HindIII and 12 units of NcoI in 100 mM Tris-HCl (pH 7.5) that contained 7 mM MgCl$_2$, 50 mM NaCl, and 7 mM 2-mercaptoethanol. After this incubation, 1 μl of a 10 μg/ml solution of RNase A was added, and the mixtures were incubated for 30 minutes at 37° C. The resultant mixtures were treated by agarose gel electrophoresis, and the portions of gel that contained DNA that was 0.9–1.5 kbp long were cut out. Each portion was treated with phenol and DNA fragments were obtained by ethanol precipitation. These DNA fragments were dissolved in 50 μl of TE.

(3) Cloning into pUC119N

To 5 μl of a solution of DNA fragments obtained as in section (1) above, 5 μl of a solution that contained 0.2 μg of plasmid pUC119C treated with NcoI and HindIII, and dephosphorylated, was added; to this mixture, 40 μl of solution A and 10 μl of solution B from the DNA ligation kit were added, and the resultant mixture was incubated for 30 minutes at 16° C. Then 10 μl of this reaction mixture was used to transform cells of E. coli JM109.

The pUC119N used was constructed by introduction of the NcoI site into the translational initiation site of commercially available pUC119 vector (Takara), and the distance between the ribosome binding site and the initiation codon was made to be eight bases.

(4) Screening of expression plasmids

The transformants obtained as described in section (2) above were transferred to a nitrocellulose filter (BA85, Schleicher & Schuel) placed on L-agar that contained 50 μg/ml ampicillin, and incubated for 5 hours at 37° C. This nitrocellulose filter was transferred to L-agar that contained 50 μg/ml ampicillin and 1 mM isopropyl-β-thiogalactoside (IPTG), and the culture was continued overnight at 37° C. The colonies that grew were brought into contact for 15 minutes with chloroform vapor and then the nitrocellulose filter was incubated for 3 hours at room temperature in a solution of 50 mM Tris-HCl (pH 7.5) that contained 150 mM NaCl, 5 mM MgCl$_2$, 3% bovine serum albumin, 80 units/ml DNase I, and 40 μg/ml lysozyme. The filter was treated first with the anti-FN monoclonal antibody FN-10 (Takara), which specifically recognizes the cell-binding domain of FN, and then with a peroxidase-labelled second antibody; then the filter was treated to develop color in the presence of hydrogen peroxide and 4-chloro-1-naphthol. Expression recombinants were selected.

In the screening that followed, 45 clones were selected from a total of 556 clones, and each was cultivated separately on 5 ml of L-broth that contained 50 μg/ml ampicillin for 5 hours at 37° C. Then 100 mM IPTG was added to the final concentration of 1 mM, and the culture was cultivated overnight at 37° C. The total protein of the bacterial cells obtained was separated by SDS-polyacrylamide gel electrophoresis (SDS-PAGE), and immunoblotting was used to check that the polypeptide produced had a molecular mass of 45 kDa to 53 kDa and that it reacted with the anti-FN monoclonal antibody FN-10.

From the above 45 clones selected, DNA sequences of the insert in the 5 clones were elucidated. These results are shown in Table 1. Of these, the plasmid that coded for the sequence of 385 amino acids from Ala$^{1133}$ to Met$^{1517}$ was named pTFB800, and cells of E. coli JM109 that carried this plasmid were named E. coli JM109/pTFB800. This strain was deposited as FERM BP-2126 at the Fermentation Research Institute of the Agency of Industrial Science and Technology, Japan.

TABLE 1

| Clone No. | Coding region (number of amino acid residues) |
|---|---|
| #001 | Tyr$^{1020}$-Met$^{1517}$ (498) |
| 003 | Gly$^{1014}$-Met$^{1517}$ (504) |
| 023 | Gly$^{1040}$-Met$^{1517}$ (478) |
| 033 | Ala$^{1133}$-Met$^{1517}$ (385) |
| 040 | Pro$^{1090}$-Met$^{1517}$ (428) |

Example 2.

Purification of peptide from recombinants

Plasmid pTFB800 that express the sequence of 385 amino acids from Ala$^{1133}$ to Met$^{1517}$ was used to transform E. coli JM109 cells, giving E. coli JM109/pTFB800 cells, and these cells were cultured overnight at 37° C. in shaking culture in 5 ml of L-broth that contained 50 μg/ml ampicillin. This culture was used to inoculate 250 ml of the same broth in a 500-ml Erlenmeyer flask, and this was cultured with agitation of 120 rpm. When the absorbance at 660 nm was 0.2, 100 mM IPTG was added to the culture broth to the final concentration of 1 mM, and the cells were harvested at 20 hours. The pellet of all bacterial cells was suspended in a solution of 50 mM Tris-HCl (pH 7.5) that contained 1 mM EDTA, and the cells were sonicated. This suspension was centrifuged and the supernatant was collected. Part of this supernatant was used for immunoblotting, in which procedure, the protein from the supernatant was separated by SDS-PAGE, and the electrophoretic pattern was transferred to a nitrocellulose membrane. Then a monoclonal antibody (FN-10, Takara) was used to check for the presence of the cell-binding domain of FN, for which this antibody is specific. After use of this first antibody, a peroxidase-labelled second antibody was used. The peroxidase activity where the second antibody had bound was color-developed in the presence of hydrogen peroxide and 4-chloro-1-naphthol, and the desired band in the vicinity of the molecular mass of 45 kDa was found. Next, the remaining part of the supernatant was put through a DEAE-Toyopearl 650S column (25 ml) equilibrated with 50 mM Tris-HCl, pH 7.5. The column was washed with 100 ml of 50 mM Tris-HCl, pH 7.5, and then first eluted with 50 ml of 50 mM Tris-HCl, pH 7.5, containing 1000 mM NaCl and then with 50 ml of 50 mM Tris-HCl, pH 7.5, containing 200 mM NaCl. Fractions were collected. The desired fractions (DEAE crude fraction) were identified by immunoblotting and pooled. The DEAE crude fraction was put through a Sepharose 4B column (10 ml) bound with monoclonal antibody FN-10. The column was washed with 50 ml of 20 mM Tris-HCl, pH 8.0, containing 100 mM NaCl, and then washed with 20 mM ammonium acetate. Elution was with 40 mM acetic acid, and fractions were collected. The desired fractions were identified by immunoblotting and pooled. By electrophoresis, about 7 mg of almost pure peptide was obtained. The amino acid sequence of the peptide was found by use of a peptide sequencer (477A/120A, Applied Biosystems Inc.) to be Ala-Ala-Pro-Ile-Val-Asn-Lys. This sequence agreed with that of the N-terminus of the desired peptide, including one residue of alanine at the N-terminus that arose from NcoI linker.

EXAMPLE 3

Measurement of cell-spreading activity

The cell-spreading activity of the polypeptide of 385 amino acid residues obtained in Example 2 and of FN was measured by the method of Ruoslahti et al. (*Methods in Enzymology*, 82, 803–831, 1981). The samples was diluted stepwise in physiological saline and distilled water, and 50 μl of the resultant solution was added to the wells of a 96-well microtitre plate, which was then incubated overnight at 4° C. in order to allow the sample to adhere to the wells. Then, phosphate-buffered saline (PBS) was used to wash the plate twice, 100 μl of 3% BSA was added to each well, and the plate was incubated for one hour at 37° C. The plate was washed twice with PBS, and then normal rat kidney (NRK-49F) cells suspended to the concentration of $10^6$ cells/ml in Eagle's Minimum Essential Medium (MEM) were added in the amount of 100 μl/well, and the plate was incubated for 2–3 hours at 37° C. The NRK-49F cells that were used were obtained as a freezed strain for storage, and first preincubated and then treated with trypsin before use. The spreading of the cells was observed under a microscope, and the minimum dose needed to have cell-spreading activity was calculated. These results are shown in Table 2.

TABLE 2

| Polypeptide (length of amino acid sequence) | | Minimum dose for cell spreading μg/well (p mole/well) | |
| --- | --- | --- | --- |
| Ala$^{1133}$-Met$^{1517}$ | (385) | 0.06 | (1.4) |
| FN | (2324) | 0.18 | (0.8) |

As explained above in detail, this invention provides a peptide which has cell-spreading activity essentially the same as that of FN, and also provides a method for its preparation by the use of genetic engineering. The polypeptides mentioned above can be used as a pharmaceutical preparation for such uses as for the healing of wounds, in collyria, for the prevention of metastases from cancer, for the implantation of artificial organs into the body, and the like. It can also be used in cosmetics, toothpaste, and the like.

What we claim is:

1. A polypeptide with cell-spreading activity which consists of the following amino acid sequence beginning with the amino terminus:

Ala Pro Ile Val Asn Lys Val Val Thr Pro Leu Ser Pro Pro
Thr Asn Leu His Leu Glu Ala Asn Pro Asp Thr Gly Val Leu
Thr Val Ser Trp Glu Arg Ser Thr Thr Pro Asp Ile Thr Gly
Tyr Arg Ile Thr Thr Thr Pro Thr Asn Gly Gln Gln Gly Asn
Ser Leu Glu Glu Val Val His Ala Asp Gln Ser Ser Cys Thr
Phe Asp Asn Leu Ser Pro Gly Leu Glu Tyr Asn Val Ser Val
Tyr Thr Val Lys Asp Asp Lys Glu Ser Val Pro Ile Ser Asp
Thr Ile Ile Pro Ala Val Pro Pro Thr Asp Leu Arg Phe
Thr Asn Ile Gly Pro Asp Thr Met Arg Val Thr Trp Ala Pro
Pro Pro Ser Ile Asp Leu Thr Asn Phe Leu Val Arg Tyr Ser
Pro Val Lys Asn Glu Glu Asp Val Ala Glu Leu Ser Ile Ser
Pro Ser Asp Asn Ala Val Val Leu Thr Asn Leu Leu Pro Gly
Thr Glu Tyr Val Val Ser Val Ser Ser Val Tyr Glu Gln His
Glu Ser Thr Pro Leu Arg Gly Arg Gln Lys Thr Gly Leu Asp
Ser Pro Thr Gly Ile Asp Phe Ser Asp Ile Thr Ala Asn Ser
Phe Thr Val His Trp Ile Ala Pro Arg Ala Thr Ile Thr Gly
Tyr Arg Ile Arg His His Pro Glu His Phe Ser Gly Arg Pro
Arg Glu Asp Arg Val Pro His Ser Arg Asn Ser Ile Thr Leu
Thr Asn Leu Thr Pro Gly Thr Glu Tyr Val Val Ser Ile Val
Ala Leu Asn Gly Arg Glu Glu Ser Pro Leu Leu Ile Gly Gln
Gln Ser Thr Val Ser Asp Val Pro Arg Asp Leu Glu Val Val
Ala Ala Thr Pro Thr Ser Leu Leu Ile Ser Trp Asp Ala Pro
Ala Val Thr Val Arg Tyr Tyr Arg Ile Thr Tyr Gly Glu Thr
Gly Gly Asn Ser Pro Val Gln Glu Phe Thr Val Pro Gly Ser
Lys Ser Thr Ala Thr Ile Ser Gly Leu Lys Pro Gly Val Asp
Tyr Thr Ile Thr Val Tyr Ala Val Thr Gly Arg Gly Asp Ser
Pro Ala Ser Ser Lys Pro Ile Ser Ile Asn Tyr Arg Thr Glu
Ile Asp Lys Pro Ser Gln Met.

* * * * *